United States Patent

Weissmüller et al.

Patent Number: 5,141,939
Date of Patent: * Aug. 25, 1992

[54] PESTICIDAL CHROMEN-6-YL-METHYL-OXY-AND-THIAPYRIZINONES

[75] Inventors: Joachim Weissmüller, Monheim; Christoph Erdelen, Leichlingen; Ulrike Wachendorff-Neumann, Monheim; Wilhelm Stendel, Wuppertal; Wolfgang Leicht, Leverkusen, all of Fed. Rep. of Germany

[73] Assignee: Bayer Aktiengesellschaft, Leverkusen, Fed. Rep. of Germany

[*] Notice: The portion of the term of this patent subsequent to Apr. 2, 2008 has been disclaimed.

[21] Appl. No.: 686,084

[22] Filed: Apr. 9, 1991

[30] Foreign Application Priority Data

Apr. 18, 1990 [DE] Fed. Rep. of Germany ....... 4012338

[51] Int. Cl.$^5$ .................. C07D 237/12; A01N 43/58
[52] U.S. Cl. ................................. 514/253; 544/230; 544/238; 544/240; 544/241; 548/517; 549/330; 549/398; 549/407
[58] Field of Search ................. 514/253; 544/238

[56] References Cited

U.S. PATENT DOCUMENTS 4,563,458 1/1986 Widdig et al. ............... 514/253
5,004,744 4/1991 Weissmuller et al. .......... 544/238

FOREIGN PATENT DOCUMENTS 0193853 9/1986 European Pat. Off.
0373425 6/1990 European Pat. Off.

OTHER PUBLICATIONS

Chem Abstr vol. 110 entry 57425m (1989).

Primary Examiner—Donald G. Daus
Attorney, Agent, or Firm—Sprung, Horn, Kramer & Woods

[57] ABSTRACT

Pesticidal substituted pyridazinones of the formula

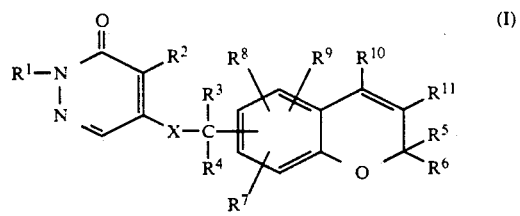

in which
R$^1$ represents alkyl, halogenolkyl, alkoxyalkyl, alkylthioalkyl, (di)alkylaminoalkyl, alkenyl or halogenoalkenyl, or represents in each case optionally substituted cycloalkyl, cycloalkylalkyl, aryl or aralkyl,
R$^2$ represents halogen or alkyl,
R$^3$ and R$^4$ independently of one another in each case represent hydrogen or alkyl,
R$^5$ and R$^6$ represent hydrogen, carboxyl, in each case optionally substituted straight-chain or branched alkyl, alkenyl, alkoxycarbonyl, aryl or aralkyl, or, together with the carbon atom to which they are bonded, rpresent an optionally substituted saturated or unsaturaated carbocyle,
R$^7$, R$^8$, R$^9$, R$^{10}$ and R$^{11}$ independently of one another in each case represent hydrogen, halogen, alkyl, halogenoalkyl, alkoxy, halogenoalkoxy, alkylthio or halogenoalkylthio, and
X represents oxygen or sulphur.

Several intermediates therefor are also new.

6 Claims, No Drawings

PESTICIDAL CHROMEN-6-YL-METHYL-OXY-AND-THIAPYRIZINONES

The invention relates to new substituted pyridazinones, to a plurality of processes for their preparation, and to their use as pesticides.

It has been disclosed that certain substituted pyridazinones such as, for example, the compound 2-t-butyl-4-chloro-5-{2-[4-(3,3-dimethylbutyl)-2,6-dichlorophenoxy]-ethylthio}-pyridazin-(2H)-3-one, the compound 2-t-butyl-4-chloro-5-(4-t-butyl-phenylmethylthio)-3(2H)pyridazinone or the compound 2-t-butyl-4-chloro-5-[2-(4-methyl-2,6-dichlorophenoxy)-ethylthio]-pyridazin-(2H)-3-one, have a good activity against pests, in particular a good insecticidal, acaricidal, nematicidal and fungicidal activity (cf., for example, EP 232,825 and EP 134,439).

However, the level of action, or duration of action, of these previously known compounds is not entirely satisfactory in all fields of application, in particular against certain organisms or when low concentrations are applied.

New substituted pyridazinones of the general formula (I)

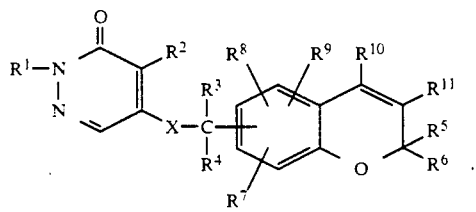

in which
R$^1$ represents alkyl, halogenoalkyl, alkoxyalkyl, alkylthioalkyl, (di)alkylaminoalkyl, alkenyl or halogenoalkenyl, or represents in each case optionally substituted cycloalkyl, cycloalkylalkyl, aryl or aralkyl,
R$^2$ represents halogen or alkyl,
R$^3$ and R$^4$ independently of one another in each case represent hydrogen or alkyl,
R$^5$ and R$^6$ represent hydrogen, carboxyl, in each case optionally substituted straight-chain or branched alkyl, alkenyl, alkoxycarbonyl, aryl or aralkyl, or, together with the carbon atom to which they are bonded, represent an optionally substituted saturated or unsaturated carbocycle,
R$^7$, R$^8$, R$^9$, R$^{10}$ and R$^{11}$ independently of one another in each case represent hydrogen, halogen, alkyl, halogenoalkyl, alkoxy, halogenoalkoxy, alkylthio or halogenoalkylthio, and
X represents oxygen or sulphur,
have been found.

It has furthermore been found that the new substituted pyridazinones of the general formula (I)

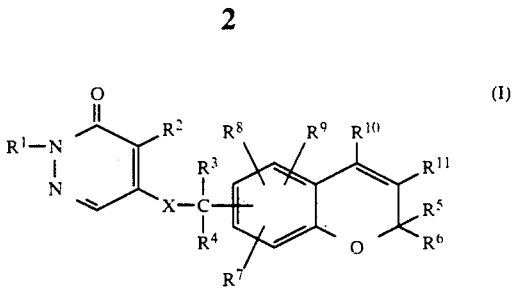

in which
R$^1$ represents alkyl, halogenoalkyl, alkoxyalkyl, alkylthioalkyl, (di)alkylaminoalkyl, alkenyl or halogenoalkenyl, or represents in each case optionally substituted cycloalkyl, cycloalkylalkyl, aryl or aralkyl,
R$^2$ represents halogen or alkyl
R$^3$ and R$^4$ independently of one another in each case represent hydrogen or alkyl,
R$^5$ and R$^6$ represent hydrogen, carboxyl, in each case optionally substituted straight-chain or branched alkyl, alkenyl, alkoxycarbonyl, aryl or aralkyl, or, together with the carbon atom to which they are bonded, represent an optionally substituted saturated or unsaturated carbocycle,
R$^7$, R$^8$, R$^9$, R$^{10}$ and R$^{11}$ independently of one another in each case represent hydrogen, halogen, alkyl, halogenoalkyl, alkoxy, halogenoalkoxy, alkylthio or halogenoalkylthio, and
X represents oxygen or sulphur,
are obtained when (a) 5-hydroxy- or 5-mercaptopyridazinones of the formula (II)

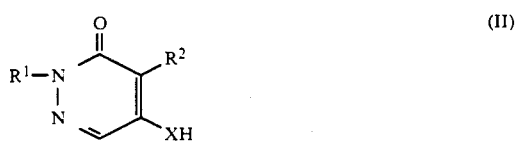

in which
X, R$^1$ and R$^2$ have the abovementioned meanings,
are reacted with alkylating agents of the formula (III)

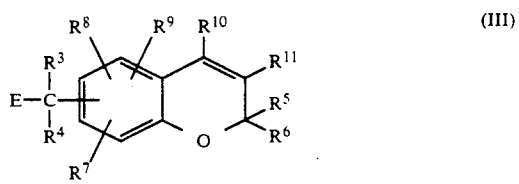

in which
E represents an electron-attracting leaving group and R$^3$, R$^4$, R$^5$, R$^6$, R$^7$, R$^8$, R$^9$, R$^{10}$ and R$^{11}$ have the above-mentioned meanings,
if appropriate in the presence of a diluent and if appropriate in the presence of a reaction auxiliary, or when (b) 5-halogenopyridazinones of the formula (IV)

in which
R$^1$ and R$^2$ have the abovementioned meanings and Hal represents halogen,
are reacted with alcohols or thiols of the formula (V)

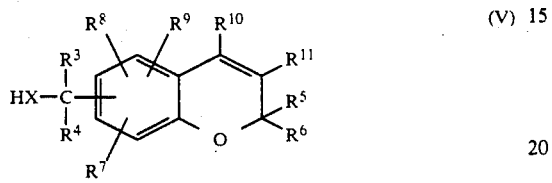

in which
R$^3$, R$^4$, R$^5$, R$^6$, R$^7$, R$^8$, R$^9$, R$^{10}$ and R$^{11}$ have the above-mentioned meanings,
if appropriate in the presence of a diluent and if appropriate in the presence of a reaction auxiliary.

Finally, it has been found that the new substituted pyridazinones of the general formula (I) have a good activity against pests, in particular a good insecticidal, acaricidal and ovicidal activity.

Surprisingly, the substituted pyridazinones according to the invention have a considerably more powerful insecticidal activity against insects and arachnids which damage plants and parasitize warm-blooded species, and additionally have a better ovicidal action, than the substituted pyridazinones known from the prior art such as, for example, the compound 2-t-butyl-4-chloro-5-{2-[4-(3,3-dimethylbutyl)-2,6-dichlorophenoxy]-ethylthio}-pyridazin-(2H)-3-one, the compound 2-t-butyl-4-chloro-5-(4-t-butyl-phenylmethylthio)-3(2H)-pyridazinone or the compound 2-t-butyl-4-chloro-5-[2-(4-methyl-2,6-dichlorophenoxy)-ethylthio]-pyridazin-3(2H)-one, which are similar compounds chemically and from the type of their action.

Formula (I) provides a general definition of the substituted pyridazinones according to the invention. Preferred compounds are those of the formula (Ia)

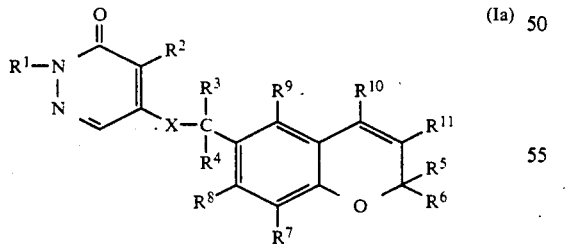

in which
R$^1$ represents straight-chain or branched alkyl having 1 to 8 carbon atoms, straight-chain or branched halogenoalkyl having 1 to 6 carbon atoms and 1 to 13 identical or different halogen atoms, in each case straight-chain or branched alkoxyalkyl, (di)alkylaminoalkyl and alkylthioalkyl having 1 to 6 carbon atoms in the respective alkyl moieties, straight-chain or branched alkenyl having 2 to 8 carbon atoms, straight-chain or branched halogenoalkenyl which has 2 to 8 carbon atoms and contains 1 to 6 halogen atoms, cycloalkyl which has 3 to 7 carbon atoms or cycloalkylalkyl which has 3 to 7 carbon atoms in the cycloalkyl moiety and 1 to 4 carbon atoms in the straight-chain or branched alkyl moiety, each of these cycloalkyl or cycloalkylalkyl radicals being optionally monosubstituted to tetrasubstituted by identical or different substituents, suitable substituents in the cycloalkyl moiety in each case being: alkyl having 1 to 4 carbon atoms and/or halogen; R$^1$ furthermore represents aryl or aralkyl which has 6 to 10 carbon atoms in the respective aryl moieties and where appropriate 1 to 4 carbon atoms in the straight-chain or branched alkyl moiety, these aryl or aralkyl radicals being optionally monosubstituted to tetrasubstituted by identical or different substituents, suitable aryl substituents being: halogen, cyano, nitro, in each case straight-chain or branched alkyl, alkoxy or alkylthio in each case having 1 to 4 carbon atoms, or in each case straight-chain or branched halogenoalkyl, halogenoalkoxy or halogenoalkylthio in each case having 1 to 4 carbon atoms and 1 to 9 identical or different halogen atoms, R$^2$ represents fluorine, chlorine, bromine or iodine, or represents straight-chain or branched alkyl having 1 to 4 carbon atoms, R$^3$ and R$^4$ independently of one another in each case represent hydrogen or straight-chain or branched alkyl having 1 to 4 carbon atoms, R$^5$ and R$^6$ independently of one another in each case represent hydrogen, in each case straight-chain or branched alkyl having 1 to 10 carbon atoms which is optionally substituted by alkoxy, carboxyl, alkoxycarbonyl or (di)alkylamino having in each case 1 to 10 carbon atoms in the alkyl moieties, or represent straight-chain or branched alkenyl having 2 to 10 carbon atoms, carboxyl, or alkoxycarbonyl having 1 to 4 carbon atoms in the alkyl moiety, phenyl or phenylalkyl which has 1 to 3 carbon atoms in the alkyl moiety and which is in each case optionally monosubstituted to trisubstituted by identical or different substituents, preferred substituents being halogen, C$_1$-C$_4$-alkyl, C$_1$-C$_4$-halogenoalkyl, C$_1$-C$_4$-alkoxy, C$_1$-C$_4$-halogenoalkoxy, C$_1$-C$_4$-alkylthio and C$_1$-C$_4$-halogenoalkylthio, or R$^5$ and R$^6$ together with the carbon atom to which they are bonded form an optionally substituted three- to seven-membered saturated or unsaturated carbocycle, R$^7$, R$^8$, R$^9$, R$^{10}$ and R$^{11}$ independently of one another in each case represent hydrogen, halogen, in each case straight-chain or branched alkyl, alkoxy or alkylthio each of which has 1 to 4 carbon atoms, or in each case straight-chain or branched halogenoalkyl, halogenoalkoxy or halogenoalkylthio in each case having 1 to 4 carbon atoms and 1 to 9 identical or different halogen atoms, and X is oxygen or sulphur.

Particularly preferred compounds of the formula (Ia) are those in which

R$^1$ represents methyl, ethyl, n- or i-propyl, n-, i-, s- or t-butyl, methoxymethyl, ethoxymethyl, methoxyethyl or ethoxyethyl, methylthiomethyl, ethylthiomethyl, methylthioethyl, ethylthioethyl, methylaminomethyl, methylaminoethyl, dimethylaminomethyl, dimethylaminoethyl, ethylaminomethyl, ethylaminoethyl, diethylaminomethyl, diethylaminoethyl, or represents halogenomethyl, halogenoethyl, n- or i-halogenopropyl, n- or i-halogenobutyl, each of which contains 1 to 3, or 1 to 5, fluorine and/or chlorine atoms, allyl, n- or i-butenyl or n- or i-pentenyl, or 2-fluoropropen-3-yl, 2-chloropropen-3-yl, 1-chloropropen-3-yl, 1,1-dichloropropen-3-yl, 1-fluoropropen-3-yl, 1,1-difluoropropen-3-yl, 1,2-dichloropropen-3-yl, 1,2-difluoropropen-3-yl, 1,1,2-trichloropropen-3-yl, or represents cyclopentyl, cyclohexyl, cyclopropylmethyl, cyclopentylmethyl, cyclopentylethyl, cyclohexylmethyl or cyclohexylethyl, each of which is optionally monosubstituted to tetrasubstituted in the cycloalkyl moiety by identical or different substituents, suitable substituents in each case being: fluorine, chlorine, bromine, methyl, ethyl, methoxy, ethoxy, halogenomethyl, halogenoethyl, halogenomethoxy or halogenoethoxy, halogen preferably representing fluorine and/or chlorine; furthermore represents phenyl, benzyl or phenethyl, each of which is optionally monosubstituted or disubstituted in the phenyl moiety by identical or different substituents, suitable substituents in each case being: fluorine, chlorine, bromine, cyano, nitro, methyl, ethyl, n- or i-propyl, n-, i-, s- or t-butyl, methoxy, ethoxy, trifuoromethyl, difluoromethyl and trifluoromethoxy, $R^2$ represents chlorine, bromine, methyl, ethyl or n- or i-propyl, $R^3$ and $R^4$ independently of one another in each case represent hydrogen, methyl or ethyl, $R^5$ and $R^6$ independently of one another in each case represent hydrogen, methyl, ethyl, n- or i-propyl, n-, i- or t-butyl, n- or i-pentyl, n- or i-hexyl, dimethoxymethyl, carboxyl, methoxycarbonyl, ethoxycarbonyl, n- or i-propoxycarbonyl, n-, i- or t-butoxycarbonyl, 2-carboxy-ethyl, 2-methoxycarbonyl-ethyl, 2-ethoxycarbonyl-ethyl, 2-t-butoxycarbonyl-ethyl, 4-carboxybutyl, 4-methoxycarbonyl-butyl, 3-diethylaminopropyl, allyl, 1,1-dimethylpropen-3-yl, 1,1-dimethylbuten-4-yl, 2-pyrrolidinyl-ethyl, or phenyl or phenylalkyl which has 1 to 3 carbon atoms in the alkyl moiety, each of these phenyl or phenylalkyl radicals being optionally monosubstituted to trisubstituted by identical or different substituents, suitable phenyl substituents in each case being: methyl, ethyl, n- or i-propyl, n-, i- or t-butyl, fluorine, chlorine, bromine, methoxy, ethoxy, trifluoromethyl, trifluoromethoxy, difluoromethoxy or trifluoromethylthio, or $R^5$ and $R^6$ together with the carbon atom to which they are bonded form a cyclopropyl, cyclopentyl, cyclohexyl, cyclohexenyl or cycloheptyl ring, each of which is optionally monosubstituted to trisubstituted by identical or different substituents, suitable substituents being: methyl, ethyl, n- or i-propyl or n-, i- or t-butyl, and $R^7$, $R^8$, $R^9$, $R^{10}$ and $R^{11}$ independently of one another in each case represent hydrogen, fluorine, chlorine, bromine, methyl, ethyl, methoxy, ethoxy, methylthio, ethylthio, trifluoromethyl, trifluoromethoxy, trifluoromethylthio or difluoromethoxy, and X represents oxygen or sulphur.

The following substituted pyridazinones of the general formula Ia

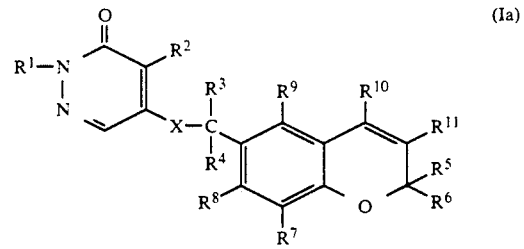

may be mentioned individually in addition to the compounds mentioned in the preparation examples:

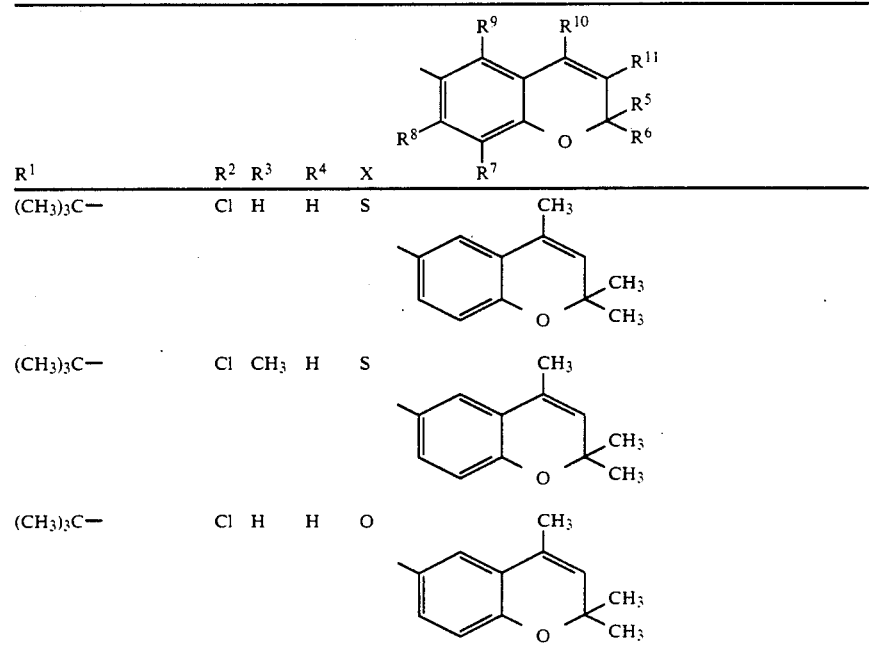

-continued
| R¹ | R² | R³ | R⁴ | X | structure |
|---|---|---|---|---|---|
| (CH₃)₃C— | Cl | H | H | S | 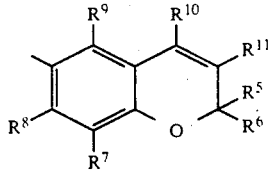 |
| (CH₃)₃C— | Cl | H | H | O | 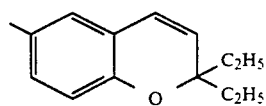 |
| (CH₃)₃C— | Cl | CH₃ | H | S | 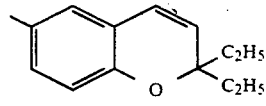 |
| (CH₃)₃C— | Cl | CH₃ | H | O | 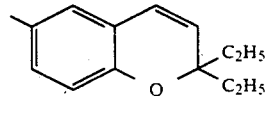 |
| (CH₃)₃C— | Cl | H | H | S | 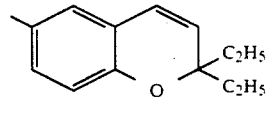 |
| (CH₃)₃C— | Cl | H | H | O | 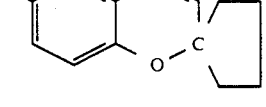 |
| (CH₃)₃C— | Cl | CH₃ | H | S | 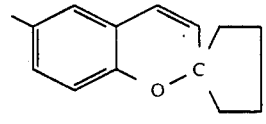 |
| (CH₃)₃C— | Cl | H | H | S | 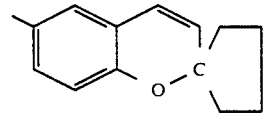 |
| (CH₃)₃C— | Cl | H | H | O | 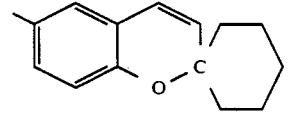 |
| (CH₃)₃C— | Cl | H | H | S | 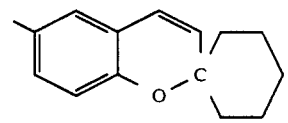 |

-continued

[Structure header: benzopyran with substituents R⁷, R⁸, R⁹, R¹⁰, R¹¹, R⁵, R⁶ around the ring system with O]

| R¹ | R² | R³ | R⁴ | X | Structure |
|---|---|---|---|---|---|
| $(CH_3)_3C-$ | Cl | H | H | O | chromene with 2-(1,1,3-trimethyl... side chain with CH₃ groups) |
| $(CH_3)_3C-$ | Cl | H | H | S | chromene with 2-(4-tert-butylcyclohexyl) |
| $(CH_3)_3C-$ | Cl | $CH_3$ | H | S | chromene with 2-(4-tert-butylcyclohexyl) |
| $(CH_3)_3C-$ | Cl | H | H | O | chromene with 2-(4-tert-butylcyclohexyl) |
| $(CH_3)_3C-$ | Br | H | H | S | chromene with 2-(4-tert-butylcyclohexyl) |
| $(CH_3)_3C-$ | Br | H | H | O | chromene with 2-(4-tert-butylcyclohexyl) |
| $(CH_3)_3C-$ | Cl | H | H | S | chromene with 2,2-bis(allyl) [$CH_2-CH=CH_2$ groups] |
| $(CH_3)_3C-$ | Cl | H | H | S | chromene with 2-methyl-2-(4-methyl-3-pentenyl) [$CH_2-CH_2-CH=C(CH_3)-CH_3$, CH₃] |
| $(CH_3)_3C-$ | Br | H | H | S | chromene with 2-methyl-2-(4-methyl-3-pentenyl) |
| $(CH_3)_3C-$ | Cl | $CH_3$ | H | S | chromene with 2-methyl-2-(4-methyl-3-pentenyl) |

-continued

![structure header: benzene ring with R9, R8, R7 substituents, R10, R11, R5, R6 and O]

| R¹ | R² | R³ | R⁴ | X | (structure) |
|---|---|---|---|---|---|
| (CH₃)₃C— | Cl | H | H | O | chromene with –CH₂–CH₂–CH=C(CH₃)–CH₃ and CH₃ at C2 |
| (CH₃)₃C— | Cl | CH₃ | H | S | 2,2-dimethyl-2H-chromene |
| (CH₃)₃C— | Br | H | H | S | 2,2-dimethyl-2H-chromene |
| (CH₃)₃C— | Br | H | H | O | 2,2-dimethyl-2H-chromene |
| (CH₃)₃C— | Cl | H | H | S | 2,2-dimethyl-2H-chromene with Cl on vinyl |
| (CH₃)₃C— | Br | H | H | S | 2,2-dimethyl-2H-chromene with Cl on vinyl |
| (CH₃)₃C— | Br | H | H | O | 2,2-dimethyl-2H-chromene with Cl on vinyl |
| (CH₃)₃C— | Br | CH₃ | H | S | 2,2-dimethyl-2H-chromene with Cl on vinyl |
| (CH₃)₃C— | Cl | H | H | S | 2,2-dimethyl-2H-chromene with Cl on aromatic ring |
| (CH₃)₃C— | Cl | H | H | S | 2,2-dimethyl-2H-chromene with Cl on aromatic ring |

-continued

| | | | | | |
|---|---|---|---|---|---|
| | | | | | ![structure with R⁹, R¹⁰, R¹¹, R⁵, R⁶, R⁷, R⁸, O, X] |
| R¹ | R² | R³ | R⁴ | X | |
| (CH₃)₃C— | Cl | H | H | S | 2,2-dimethyl-chromene with Cl |
| dichlorocyclopropyl-CH₂— | Cl | H | H | S | 2,2-dimethyl-chromene |
| dichlorocyclopropyl-CH₂— | Cl | H | H | O | 2,2-dimethyl-chromene |
| (CH₃)C(H)=CH—CH₂— (isobutenyl) | Cl | H | H | S | 2,2-dimethyl-chromene |
| cyclohexyl- | Cl | H | H | S | 2,2-dimethyl-chromene |
| ClCH=CH—CH₂— | Cl | H | H | S | 2,2-dimethyl-chromene |
| ClCH=CH—CH₂— | Br | H | H | S | 2,2-dimethyl-chromene |
| ClCH=CH—CH₂— | Cl | H | H | O | 2,2-dimethyl-chromene |
| FCH=CH—CH₂— | Cl | H | H | S | 2,2-dimethyl-chromene |
| Cl—C(CH₃)₂—CH₂— | Cl | H | H | S | 2,2-dimethyl-chromene |
| Cl—C(CH₃)₂—CH₂— | Br | H | H | S | 2,2-dimethyl-chromene |

-continued
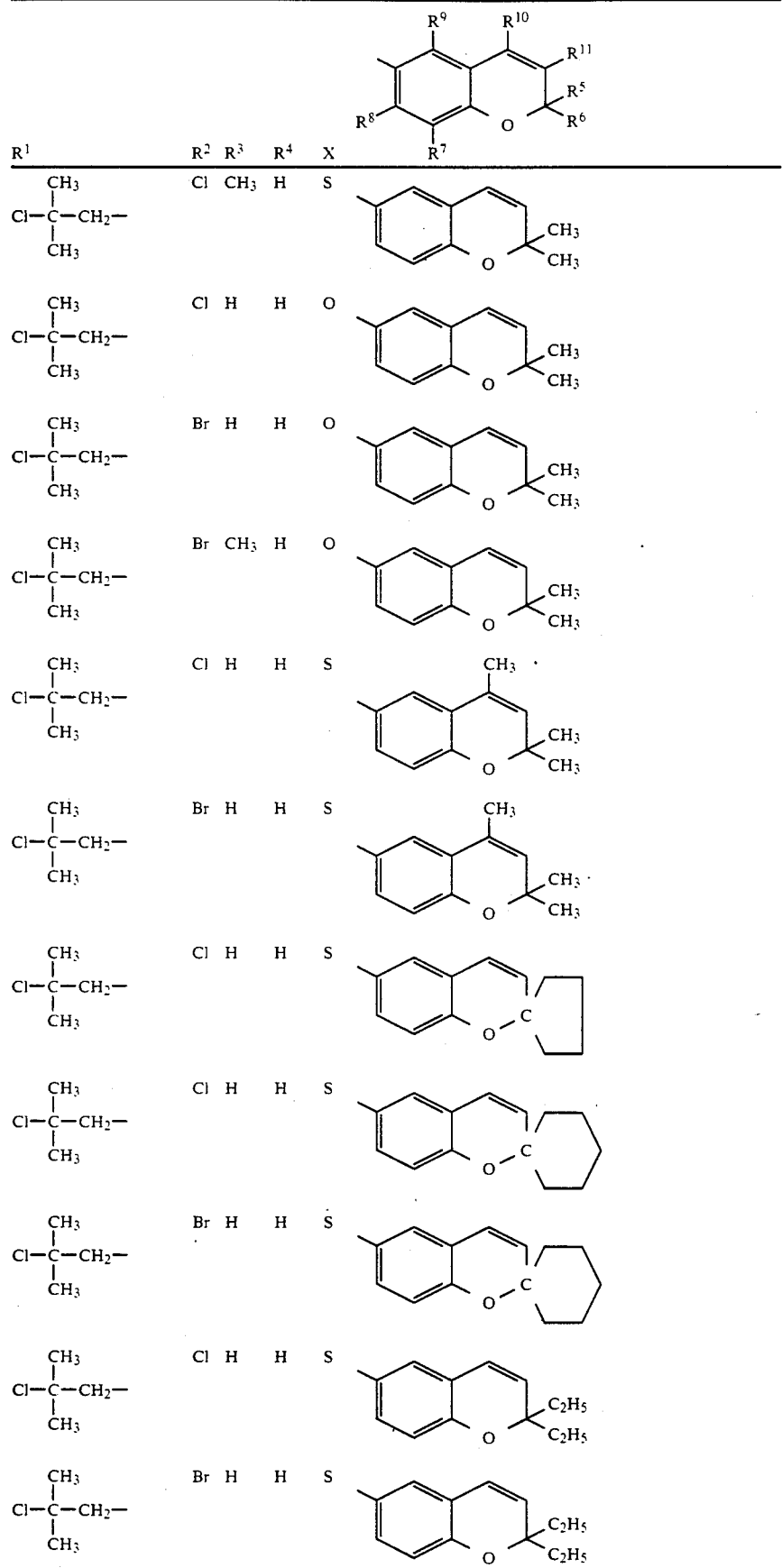

-continued

| R¹ | R² | R³ | R⁴ | X | (chromene structure) |
|---|---|---|---|---|---|
| Cl-C(CH₃)₂-CH₂- | Br | H | H | O | 6-position; 2,2-diethyl |
| Cl-C(CH₃)₂-CH₂- | Cl | H | H | S | 4-Cl; 2,2-dimethyl |
| (CH₃)₃C- | Cl | H | H | S | 2-methyl-2-[(CH₂)₃N(C₂H₅)₂] |
| (CH₃)₃C- | Cl | H | H | S | 2-methyl-2-COOCH₃ |
| (CH₃)₃C- | Cl | H | H | S | 2-CH(CH₃)₂, 2-H |
| (CH₃)₃C- | Cl | H | H | S | 2-H, 2-C(CH₃)₂CH₃ (t-Bu-CH) |
| (CH₃)₃C- | Cl | H | H | S | 2-(4-chlorophenyl) |
| (CH₃)₃C- | Cl | H | H | S | 2-(4-tert-butylphenyl) |
| (CH₃)₃C- | Cl | H | H | S | 2-(4-methylphenyl) |

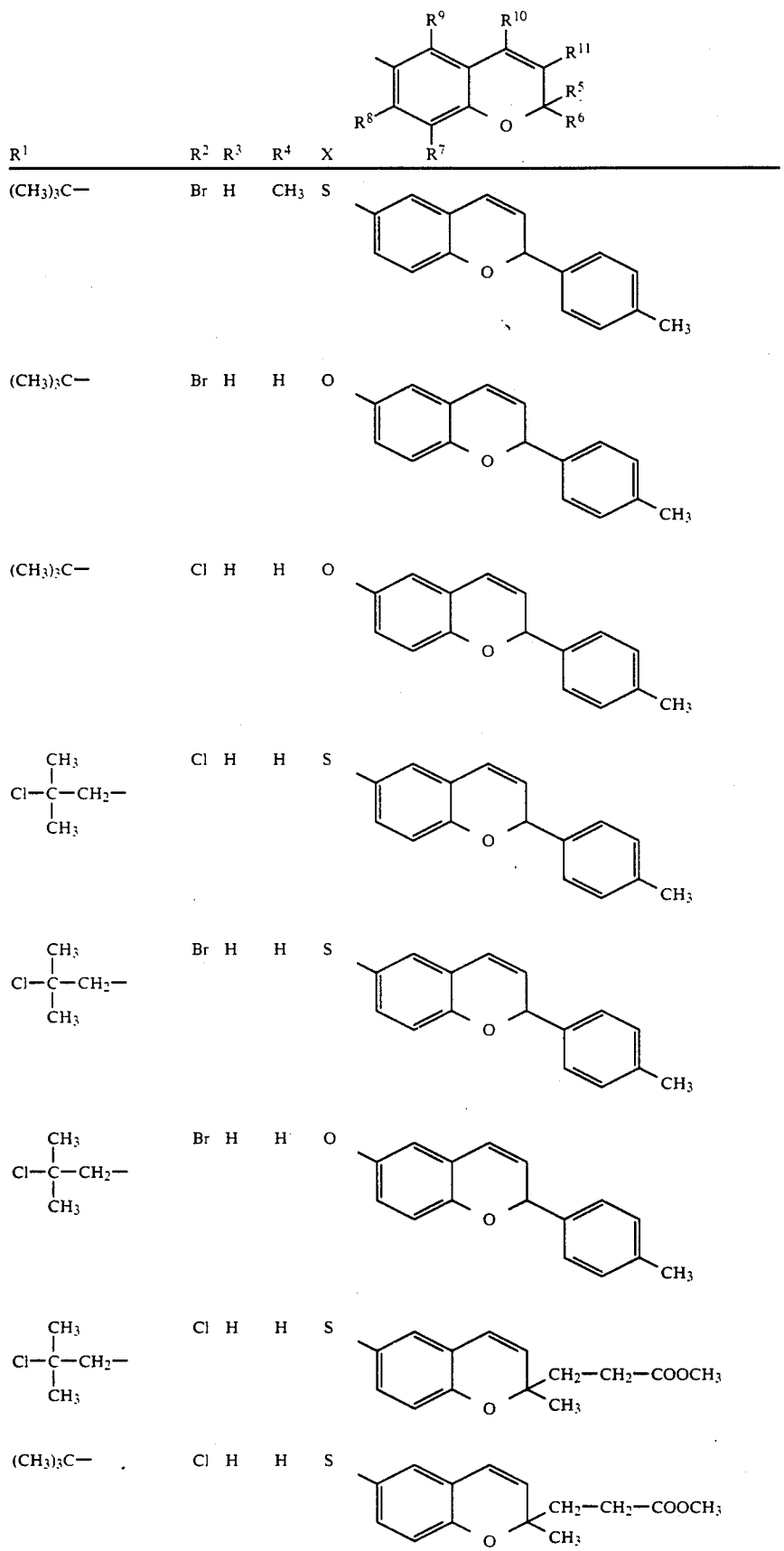

-continued

| R¹ | R² | R³ | R⁴ | X | structure |
|---|---|---|---|---|---|
| (CH₃)₃C— | Cl | H | H | S | |
| (CH₃)₃C— | Br | H | H | S | |
| (CH₃)₃C— | Cl | H | H | O | |
| (CH₃)₃C— | Br | H | H | O | |
| (CH₃)₃C— | Br | CH₃ | H | S | |
| Cl—C(CH₃)₂—CH₂— | Cl | H | H | S | |
| Cl—C(CH₃)₂—CH₂— | Cl | H | H | O | |
| Cl—C(CH₃)₂—CH₂— | Br | H | H | S | |

-continued

| R¹ | R² | R³ | R⁴ | X | 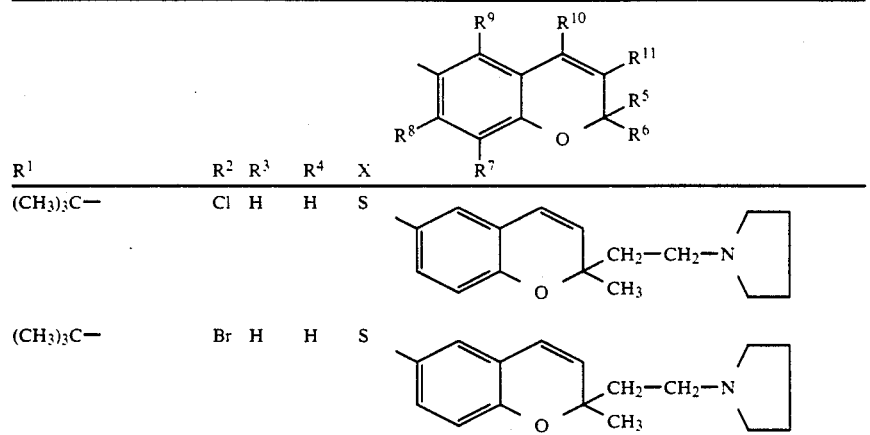 |
|---|---|---|---|---|---|
| (CH₃)₃C— | Cl | H | H | S | |
| (CH₃)₃C— | Br | H | H | S | |

If, for example, 2-t-butyl-4-chloro-5-hydroxypyridazin-3-(2H)-one and 6-chloromethyl-2,2-dimethyl-(2H)-chromene are used as starting substances, the course of the reaction of process (a) according to the invention may be represented by the following equation:

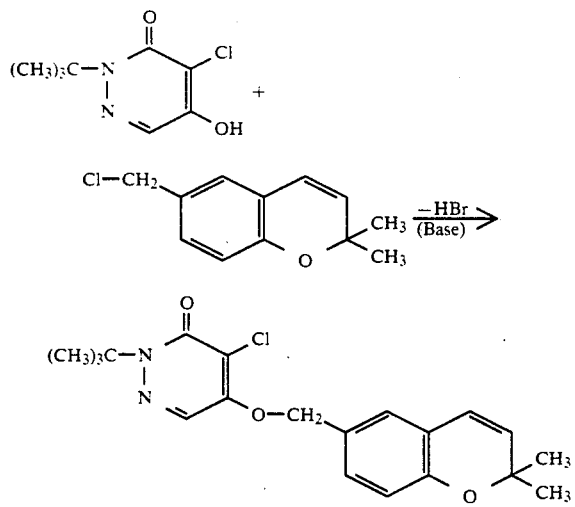

If, for example, 2-cyclopropylmethyl-4,5-dichloropyridazin-3-(2H)-one and 6-mercaptomethyl-2,2-dimethyl-(2H)-chromene are used as starting substances, the course of the reaction of process (b) according to the invention may be represented by the following equation:

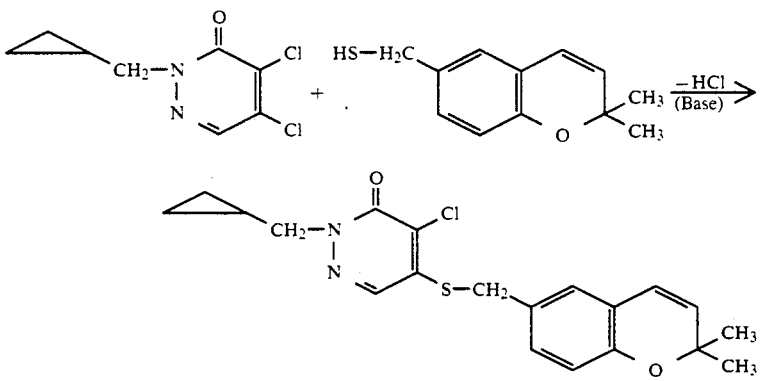

Formula (II) provides a general definition of the 5-hydroxy- or 5-mercaptopyridazinones required as starting substances for carrying out process (a) according to the invention. In this formula (II), R¹, R² and X preferably represent those radicals which have already been mentioned in connection with the description of the substances of the formula (I) according to the invention as being preferred for these substituents.

The 5-hydroxy- and 5-mercaptopyridazinones of the formula (II) are known or can be obtained in analogy to known processes (cf., for example, EP 302,346; EP 183,212; Chem. Pharm. Bull. 18, 147–156 [1979]; JP 61/109777; Heterocycles 26, 1–4 [1987]; Pestic. Sci. 9, 571–581 [1978]; Chem. Zvesti 30, 663–673 [1976] or CA 87: 135236y; CS 146172 dated 15.12.1972).

Formula (III) provides a general definition of the alkylating agents furthermore required as starting substances for carrying out process (a) according to the invention. In this formula (III), R³, R⁴, R⁵, R⁶, R⁷, R⁸, R⁹, R¹⁰ and R¹¹ preferably represent those radicals which have already been mentioned in connection with the description of the substances of the formula (I) according to the invention as being preferred for these substituents.

E represents a leaving radical customary in alkylating agents, preferably halogen, in particular chlorine, bromine or iodine, or represents in each case optionally substituted alkylsulphonyloxy, alkoxysulphonyloxy or arylsulphonyloxy such as, in particular, methanesulphonyloxy, trifluoromethanesulphonyloxy, methoxysulphonyloxy, ethoxysulphonyloxy or p-toluenesulphonyloxy.

The alkylating agents of the formula (III) are generally known compounds or can be obtained in analogy to generally known processes of organic chemistry (cf. DE-OS (German Published Specification) 2,450,193, Czechoslovak Patent 252,601—cited in Chem. Abstr. 110, 57425).

The alkylating agents of the formula (III)

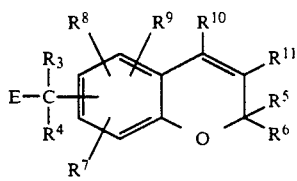

(III)

in which

R$^3$ and R$^4$ independently of one another in each case represent hydrogen or straight-chain or branched alkyl having 1 to 4 carbon atoms, R$^5$ and R$^6$ independently of one another in each case represents hydrogen, in each case straight-chain or branched alkyl having 1–10 carbon atoms which is optionally substituted by alkoxy, carboxyl, alkoxycarbonyl or (di)alkylamino having in each case 1 to 10 carbon atoms, or straight-chain or branched alkenyl having 2–10 carbon atoms, or carboxyl, alkoxycarbonyl which has 1 to 4 carbon atoms in the alkyl moiety, or phenyl or phenylalkyl which has 1 to 3 carbon atoms in the alkyl moiety, the phenyl and phenylalkyl radicals being in each case optionally monosubstituted to trisubstituted by identical or different substituents, or R$^5$ and R$^6$ together with the carbon atom to which they are bonded form an optionally substituted three- to seven-membered saturated or unsaturated carbocycle, R$^7$, R$^8$, R$^9$, R$^{10}$ and R$^{11}$ independently of one another in each case represent hydrogen, halogen, in each case straight-chain or branched alkyl, alkoxy or alkylthio in each case having 1 to 4 carbon atoms, or in each case straight-chain or branched halogenoalkyl, halogenoalkoxy, or halogenoalkylthio in each case having 1 to 4 carbon atoms and 1 to 9 identical or different halogen atoms, and E represents halogen such as, preferably, chlorine, bromine or iodine, or also represents in each case optionally substituted alkylsulphonyloxy, alkoxysulphonyloxy or arylsulphonyloxy such as, preferably, methanesulphonyloxy, trifluoromethanesulphonyloxy, methoxysulphonyloxy, ethoxysulphonyloxy or p-tolyl sulphonyloxy, with the exception of 6-chloromethyl-2H-1-benzopyran and 6-(1-bromopropyl)-2,2-dimethyl-2H-1-benzopyran, were hitherto unknown.

The alkylating agents of the formula (III) are obtained in analogy to generally known processes by reacting corresponding alcohols of the formula (V)

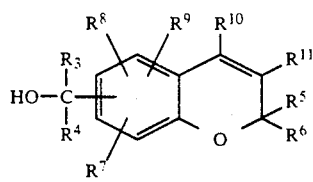

(V)

in which

R$^3$ and R$^4$ independently of one another in each case represent hydrogen or straight-chain or branched alkyl having 1 to 4 carbon atoms, R$^5$ and R$^6$ independently of one another in each case represents hydrogen, in each case straight-chain or branched alkyl having 1 to 10 carbon atoms which is optionally substituted by alkoxy, carboxyl, alkoxycarbonyl or (di)alkylamino having in each case 1 to 10 carbon atoms in the alkyl moieties or straight-chain or branched alkenyl having 2 to 10 carbon atoms, or carboxyl, or alkoxycarbonyl which has 1 to 4 carbon atoms in the alkyl moiety, or phenyl or phenylalkyl which has 1 to 3 carbon atoms in the alkyl moiety, the phenyl and phenylalkyl radicals being in each case optionally monosubstituted to trisubstituted by identical or different substituents, or R$^5$ and R$^6$ together with the carbon atom to which they are bonded form an optionally substituted three- to seven-membered saturated or unsaturated carbocycle, R$^7$, R$^8$, R$^9$, R$^{10}$ and R$^{11}$ independently of one another in each case represent hydrogen, halogen, in each case straight-chain or branched alkyl, alkoxy or alkylthio in each case having 1 to 4 carbon atoms, or in each case straight-chain or branched halogenoalkyl, halogenoalkoxy, or halogenoalkylthio in each case having 1 to 4 carbon atoms and 1 to 9 identical or different halogen atoms, with appropriate halogenation or sulphonylation agents (cf. also the preparation examples).

The alcohols of the formula (III) are known in some cases or can be obtained in analogy to generally known processes of organic chemistry (cf. Indian J. Chem. 23B, 1124 (1984); Liebigs Ann. Chem. 1986, 799; Indian J. Chem. 17B, 73 (1979); Houben-Weyl IX, 7–19; J. Nat. Prod. 49 (1), 143).

The alcohols of the formula (Va)

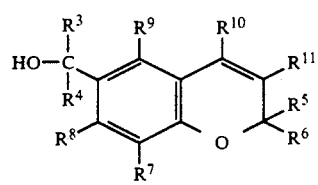

(Va)

in which

R$^3$ and R$^4$ independently of one another in each case represent hydrogen or straight-chain or branched alkyl having 1 to 4 carbon atoms, R$^5$ and R$^6$ independently of one another in each case represent hydrogen, in each case straight-chain or branched alkyl having 1 to 10 carbon atoms which is optionally substituted by alkoxy, carboxyl, alkoxycarbonyl or (di)alkylamino having in each case 1 to 10 carbon atoms in the alkyl moieties, or straight-chain or branched alkenyl having 2 to 10 carbon atoms, or carboxyl, alkoxycarbonyl which has 1 to 4 carbon atoms in the alkyl moiety, or phenyl or phenylalkyl which has 1 to 3 carbon atoms in the alkyl moiety, the phenyl and phenylalkyl radicals being in each case optionally monosubstituted to trisubstituted by identical or different substituents, or $R^5$ and $R^6$ together with the carbon atom to which they are bonded form an optionally substituted three- to seven-membered saturated or unsaturated carbocycle, $R^7$, $R^8$, $R^9$, $R^{10}$ and $R^{11}$ independently of one another in each case represent hydrogen, halogen, in each case straight-chain or branched alkyl, alkoxy or alkylthio in each case having 1 to 4 carbon atoms, or in each case straight-chain or branched halogenoalkyl, halogenoalkoxy, or halogenoalkylthio in each case having 1 to 4 carbon atoms and 1 to 9 identical or different halogen atoms, with the proviso that $R^7$, $R^8$ or $R^9$ do not represent methoxy, or $R^7$, $R^8$, $R^9$, $R^{10}$ and $R^{11}$ do not represent hydrogen if $R^5$ and $R^6$ represent methyl, were hitherto unknown.

The alcohols of the formula (Va) are obtained in analogy to generally known processes by reducing appropriately substituted carbonyl compounds of the formula (VI)

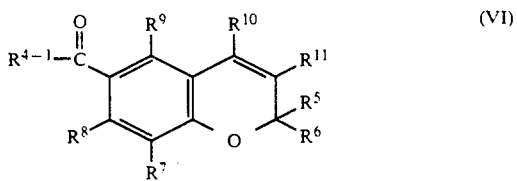

in which $R^{4\cdot 1}$ represents hydrogen, in each case straight-chain or branched alkyl or alkoxy having 1 to 4 carbon atoms, or hydroxyl, and $R^5$, $R^6$, $R^7$, $R^8$, $R^9$, $R^{10}$ and $R^{11}$ have the abovementioned meanings, preferably by means of complex metal hydrides such as, for example, sodium borohydride or lithium aluminum hydride, or reacting them with Grignard compounds of the general formula (VII)

in which $R^3$ and Hal have the abovementioned meanings, in a manner known per se.

The carbonyl compounds of the formula (VI) are known or can be prepared in analogy to known processes (cf. Bull. Chem. Soc. Jpn. 57, 442 (1984); Indian J. Chem. 17B, 73 (1979); Angew. Chem. 94, 254 (1982).

Formula (IV) provides a general definition of the 5-halogenopyridazinones required as starting substances for carrying out process (b) according to the invention. In this formula (IV), Hal preferably represents chlorine and bromine and $R^1$ and $R^2$ preferably represent those radicals which have already been mentioned in connection with the description of the substances of the formula (I) according to the invention as being preferred for these substituents.

The 5-halogenopyridazinones of the formula (IV) are known or can be obtained in analogy to known processes (cf., for example, EP 169,375; EP 302,346; Chem. Zvesti 38, 239–246 [1984] or CA 101: 110848u; GB 2095 669; Synthesis 1981, 631–633.)

Formula (V) provides a general definition of the alcohols and thiols furthermore required as starting substances for carrying out process (b) according to the invention. Preferred starting substances of the formula (V) are those in which $R^3$, $R^4$, $R^5$, $R^6$, $R^7$, $R^8$, $R^9$, $R^{10}$ and $R^{11}$ and X preferably represent those radicals which have already been mentioned in connection with the description of the substances of the formula (Ia) according to the invention as being preferred for these substituents.

The intermediates which the invention comprises, for the preparation of the active compounds of the general formula (I) according to the invention according to preparation processes (a) and (b), are the new alkylating agents of the formula (III) and the new chromenylalkyl alcohols of the formula (Va).

Suitable diluents for carrying out processes (a) and (b) according to the invention are inert organic solvents. These include, in particular, aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform, carbon tetrachloride, ethers such as diethyl ether, dioxane, tetrahydrofuran or ethylene glycol dimethyl ether or ethylene glycol diethyl ether, ketones such as acetone or butanone, nitriles such as acetonitrile or propionitrile, amides such as dimethylformamide, dimethylacetamide, N-methylformanilide, N-methylpyrrolidone or hexamethylphosphoric triamide, esters such as ethyl acetate, or sulphoxides, such as dimethyl sulphoxide.

If appropriate, the processes (a) and (b) according to the invention can also be carried out in a two-phase system such as, for example, water/toluene or water/dichloromethane, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}$/$C_{15}$-alkylammonium chloride, dibenzyl-dimethyl-ammonium methylsulphate, dimethyl-$C_{12}$/$C_{14}$-alkyl-benzylammonium chloride, tetrabutylammonium hydroxide, 15-crown-5, 18-crown-6, triethylbenzylammonium chloride, trimethylbenzylammonium chloride or tris-[2-(2-methoxyethoxy)-ethyl]-amine.

Processes (a) and (b) according to the invention are preferably carried out in the presence of a suitable reaction auxiliary. Suitable reaction auxiliaries are all inorganic and organic bases which can customarily be used. The following are preferably used: hydrides, hydroxides, amides, alcoholates, carbonates or hydrogen carbonates of alkali metals such as, for example, sodium hydride, sodium amide, sodium hydroxide, sodium methylate, sodium ethylate, potassium t-butylate, sodium carbonate or sodium hydrogen carbonate, and also tertiary amines such as, for example, triethylamine, N,N-dimethylaniline, pyridine, N,N-dimethylaminopyridine, diazabicyclooctane (DABCO), diazabicyclononene (DBN) or diazabicycloundecene (DBU).

When carrying out processes (a) and (b) according to the invention, the reaction temperatures can be varied within a substantial range. In general, the processes are carried out at temperatures between 0° C. and 150° C., preferably at temperatures between 20° C. and 120° C.

For carrying out process (a) according to the invention, 1.0 to 5.0 moles, preferably 1.0 to 3.0 moles, of alkylating agent of the formula (III) and, if appropriate, 1.0 to 5.0 moles, preferably 1.0 to 3.0 moles, of reaction auxiliary are generally employed per mole of 5-hydroxy- or 5-mercaptopyridazinone of the formula (II).

The reaction is carried out and the reaction products are worked up and isolated by generally customary methods (cf. also the Preparation Examples).

For carrying out process (b) according to the invention, 1.0 to 5.0 moles, preferably 1.0 to 3.0 moles, of alcohol or thiol of the formula (V) and, if appropriate, 1.0 to 5.0 moles, preferably 1.0 to 3.0 moles, of reaction auxiliary are generally employed per mole of 5-halogenopyridazinone of the formula (IV).

The reaction is carried out and the reaction products are worked up and isolated by generally customary methods.

The active compounds are suitable for combating animal pests, preferably arthropods and nematodes, in particular insects and arachnids, encountered in agriculture, in animal husbandry, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera* spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus. Gryllotalpa spp., Locusta migratoria migratorioides, Melanoplus differentialis* and *Schistocerca gregaria.* From the order of the Dermaptera, for example, *Forficula auricularia.* From the order of the Isoptera, for example, *Reticulitermes spp.* From the order of the Anoplura, for example, *Phylloxera vastatrix, Pemphigus spp., Pediculus humanus corporis, Haematopinus spp.* and *Linognathus spp.* From the order of the Mallophaga, for example, *Trichodectes spp.* and *Damalinea spp.* From the order of the Thysanoptera, for example, *Hercinothrips femoralis* and *Thrips tabaci.* From the order of the Heteroptera, for example, *Eurygaster spp., Dysdercus intermedius, Piesma quadrata, Cimex lectularius, Rhodnius prolixus* and *Triatoma spp.* From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. Psylla spp.* From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varive stis, Atomaria spp., Oryzaephilus surinamensis, Antho nomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Cono derus spp., Melolontha melolontha, Amphimallon solsti tialis* and *Costelytra zealandica.* From the order of the Hymenoptera, for example, *Diprion spp., Hoplocampa spp., Lasius spp., Monomorium pharaonis* and *Vespa spp.* From the order of the Diptera, for example, *Aedes spp., Anopheles spp., Culex spp., Drosophila melanogaster, Musca spp., Hydrotaea spp., Haematobia spp., Glossina spp., Melophagus spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphonaptera, for example, *Xenopsylla cheopis, Ceratophyllus spp.* and *Ctenocephalides spp.* From the order of the Arachnida, for example, *Scorpio maurus* and *Latrodectus mactans.*

From the order of the Acarina, for example, *Acarus siro, Argas spp., Ornithodoros spp., Dermanyssus gallinae, Ornithonyssus spp., Eriophyes ribis, Phyllocoptruta oleivora, Boophilus spp., Rhipicephalus spp., Amblyomma spp., Hyalomma spp., Ixodes spp., Dermacentor spp., Haemaphysalis spp., Otobius spp., Psoroptes spp., Choriop tes spp., Sarcoptes spp., Psorergates spp., Demodex spp., Notoedres spp., Tarsonemus spp., Bryobia praetiosa, Panonychus spp.* and *Tetranychus spp.*

The active compounds according to the invention are not only active against plant, hygiene and stored-product pests, but also, in the veterinary medicine sector, against animal parasites (ectoparasites and endoparasites), such as scaly ticks, argasidae, scab mites, trombidae, flies (stinging and licking), parasitic fly larvae, lice, hair lice, bird lice, fleas and worms which live as endoparasites. They are active against normally sensitive and resistant species and strains, as well as against all parasitic and non-parasitic stages of development of the ecto- and endoparasites.

The active substances according to the invention are distinguished by a high insecticidal and acaricidal activity.

They can be employed with particularly good success for combating insects which are harmful to plants such as, for example, against the larvae of the mustard beetle (*Phaedon cochleariae*) or against the larvae of the cabbage moth (*Plutella xylostella*) or against the larvae of the green rice leaf hopper (*Nephotettix cincticeps*) or against the larvae of the armyworm (*Spodoptera frugi-*

*perda*); for combating mites which are harmful to plants such as, for example, against the common spider mite or the greenhouse red spider mite (*Tetranychus urticae*).

Moreover, they can be employed with particularly good success for combating pests which live as parasites on warm-blooded species such as, for example, against the larvae of the sheep maggot fly (*Lucilia cuprina*), against cattle ticks (*Boophilus microplus*) or against scab mites (*Psoroptes ovis*).

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, furthermore to formulations used with burning equipment, such as fumigating cartridges, fumigating cans, fumigating coils and the like, as well as to ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose, natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored-product pests, the active compounds are distinguished by an excellent residual action on wood and clay as well as a good stability to alkali on limed substrates.

The active compounds according to the invention are also suitable for combating insects, mites, ticks etc., in the sectors of animal keeping and cattle breeding; better results, for example higher milk production, greater weight, more attractive animal pelt, longer life etc., can be achieved by combating the pests.

The application of the active compounds according to the invention occurs in this sector in a known fashion, such as by external application in the form of, for example, dipping, spraying, pouring-on, spotting-on and dusting, as well as by parenteral application in the form, for example, of injection, and, furthermore, by means of the feed-through process. In addition, application as molded articles (collar, ear tag) and application in the form of the so-called "environment treatment" are also possible.

The biological effectiveness of the compounds according to the invention will be explained with reference to the examples below.

Preparation Examples

EXAMPLE 1

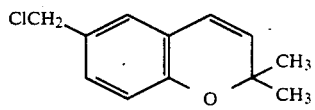

1.4 g (0.01 mol) of potassium carbonate is added in portions at 10° C. to a solution of 2.4 g (0.011 mol) of 2-tert.-butyl-4-chloro-5-mercapto-3(2H)-pyridazinone· and 2.4 g (0.012 mol) of 6-chloromethyl-2,2,-dimethyl-(2H)-chromene in 50 ml of dioxane, and the mixture is subsequently stirred for 16 hours at room temperature (20° C.). The reaction mixture is subsequently diluted with 300 ml of water and extracted three times using 100 ml of methylene chloride each time. The organic phase is dried over sodium sulphate and evaporated. After the residue has been chromatographed over silica gel 60 using methylene chloride, 1.9 g (48% of theory) of 2-tert.-butyl-4-chloro-5-[(2,2-dimethyl-(2H)-chromen-6-yl)-methylthio]-3(2H)-pyridazinone are obtained.

$^1$H-NMR (δppm, CDCl$_3$):
7.62 (1H, s), 7.1 (1H, dd), 7.0 (1H, d), 6.75 (1H, d), 6.3 (1H, d), 5.65 (1H, d), 4.17 (2H, s), 1.63 (9H, s), 1.43 (6H, s).

Preparation of the starting compounds of the formula (II)

EXAMPLE (II-1)

5.6 g (0.047 mol) of thionyl chloride are added dropwise to a solution of 5 g (0.026 mol) of 6-hydroxymethyl-2,2-dimethyl-(2H)-chromene in 100 ml of methylene chloride, and the mixture is stirred for 16 hours at 40° C. The reaction mixture is poured into 150 ml of water, and the organic phase is separated off, dried over sodium sulphate and evaporated.

5.3 g (98% of theory) of 6-chloromethyl-2,2-dimethyl-(2H)-chromene are obtained.

$^1$H-NMR (CDCl$_3$, δppm):
7.1 (dd, 1H), 7.0 (d, 1H), 6.73 (d, 1H), 6.29 (d, 1H), 5.6 (d, 1H), 4.5 (s, 2H), 1.42 (s, 6H).

USE EXAMPLES

In the Use Examples which follow, the compounds listed below were employed as comparison substances:

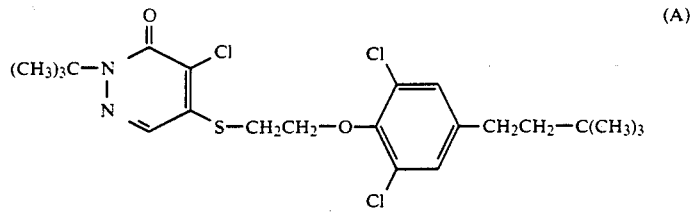
(A)

2-t-butyl-4-chloro-5-(2-[4-(3,3-dimethyl-butyl)-2,6-dichlorophenoxy]-ethylthio-3(2H)-pyridazinone (disclosed in EP 232,825)

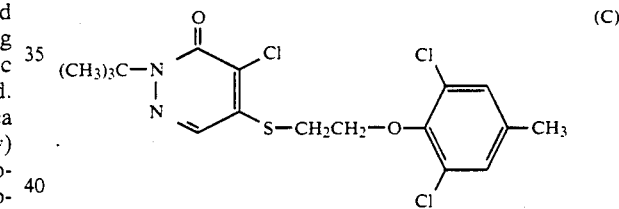
(B)

2-t-butyl-4-chloro-5-(4-t-butyl-phenylmethylthio)-3(2H)-pyridazinone (disclosed in EP-A 134,439)

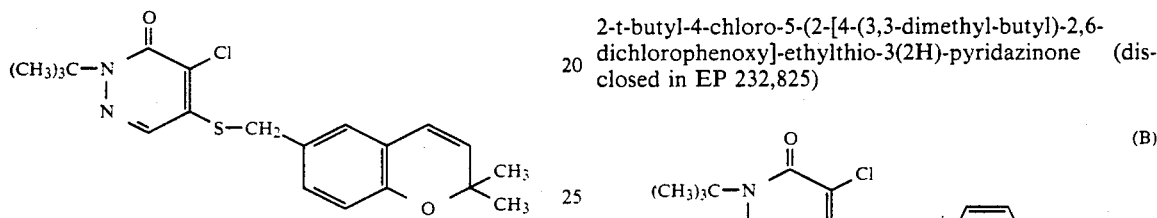
(C)

2-t-butyl-4-chloro-5-[2-(4-methyl-2,6-dichlorophenoxy)-ethylthio]-3(2H)-pyridazinone (disclosed in EP-A 232,825).

EXAMPLE A

Phaedon larvae test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) while the leaves are still moist.

After the desired period of time, the destruction in % is determined. 100% means that all the beetle larvae have been killed; 0% means that none of the beetle larvae have been killed.

A superior activity compared with the prior art is shown in this test, for example, by the compound of Preparation Example (1).

EXAMPLE B

Plutella test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the desired period of time, the destruction in % is determined. 100% means that all the caterpillars have been killed; 0% means that none of the caterpillars have been killed.

A superior activity compared with the prior art is shown in this test, for example, by the compound of Preparation Example (1).

EXAMPLE C

Spodoptera test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera frugiperda*), while the leaves are still moist.

After the desired period of time, the destruction in % is determined. 100% means that all the caterpillars have been killed; 0% means that none of the caterpillars have been killed.

A superior activity compared with the prior art is shown in this test, for example, by the compound of Preparation Example (1).

EXAMPLE D

Nephotettix test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with the green rice leaf hopper (*Nephotettix cincticeps*), while the seedlings are still moist.

After the desired period of time, the destruction in % is determined. 100% means that all the leaf hoppers have been killed; 0% means that none of the leaf hoppers have been killed.

A superior activity compared with the prior art is shown in this test, for example, by the compound of Preparation Example (1).

EXAMPLE E

Tetranychus test (resistant)

Solvent 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested by all development stages of the common spider mite or greenhouse red spider mite (*Tetranychus urticae*), are treated by being dipped into the active compound preparation of the desired concentration.

After the desired period of time, the destruction in % is determined. 100% means that all the spider mites have been killed; 0% means that none of the spider mites have been killed.

A superior activity compared with the prior art is shown in this test, for example, by the compound of Preparation Example (1).

EXAMPLE F

Test with *Lucilia cuprina* resistant larvae

Emulsifier: 35 parts by weight of ethylene glycol monomethyl ether
35 parts by weight of nonylphenol polyglycol ether To produce a suitable preparation of active compound, three parts by weight of active compound are mixed with seven parts by weight of the abovementioned mixture and the concentrate thus obtained is diluted with water to the particular desired concentration.

About 20 *Lucilia cuprina* res. larvae are introduced into a test tube which contains approx. 1 cm$^3$ of horse meat and 0.5 ml of the preparation of active compound. After 24 hours, the degree of destruction is determined.

A superior activity compared with the prior art is shown in this test, for example, by the compound of Preparation Example (1).

EXAMPLE G

Tick test (*Boophilus microplus*)/Inhibition of egg deposition

Solvent: 35 parts by weight of ethylene glycol monomethyl ether
35 parts by weight of nonylphenol polyglycol ether To prepare a suitable formulation, three parts by weight of active compound are mixed with seven parts of the abovementioned solvent/emulsifier mixture, and the resulting emulsion concentrate is diluted with water to the particular desired concentration.

Adult female ticks of the species Boophilus microplus (sensitive or resistant) which have sucked themselves full are immersed for one minute in this preparation of active compound. After groups of 10 female specimens of the various tick species have been immersed, they are transferred into Petri dishes where the bottom is covered with a filter disc of the appropriate size.

After 10 days, the effectiveness of the preparation of active compound is determined by recording the inhibition of egg deposition compared with untreated control ticks. The action is expressed in percent, and 100% means that eggs were no longer deposited and 0% means that the ticks deposited eggs in normal amounts.

A superior activity compared with the prior art is shown in this test, for example, by the compound of Preparation Example (1).

EXAMPLE H (Test with Psoroptes ovis)

Solvent: 35 parts by weight of ethylene glycol monomethyl ether
35 parts by weight of nonylphenol polyglycol ether Test object Natural population (larvae, nymphs, adults) of Psoroptes ovis which had been sampled 1 hour before the test by scraping the skin of naturally infested cattle.

Testing procedure

Depending on the concentration, 10-25 mites are transferred into the use dilution to be tested, 10 and 1 ppm.

Storage in a climatized test chamber (28° C.±1° C., 80% relative humidity±10%).

The action is checked after 24 hours using a stereomicroscope, magnification 12.5 x.

Criterion

3 = 100% action = all mites are destroyed
2 = >50% action = more than 50% of the mites are destroyed
1 = <50% of action = less than 50% of the mites are destroyed
0 = 0% action = all mites are alive A superior activity compared with the prior art is shown in this test, for example, by the compound of Preparation Example (1).

It will be understood that the specification and examples are illustrative but not limitative of the present invention and that other embodiments within the spirit and scope of the invention will suggest themselves to those skilled in the art.

We claim:

1. A substituted pyridazinone of the formula

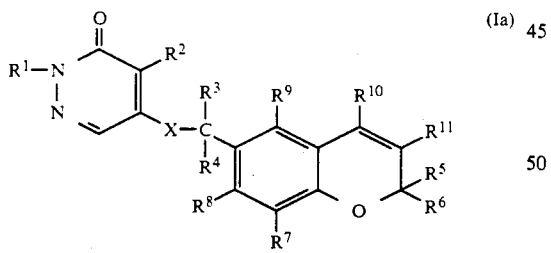

in which
$R^1$ represents straight-chain or branched alkyl having 1 to 8 carbon atoms, straight-chain or branched halogenoalkyl having 1 to 6 carbon atoms and 1 to 13 identical or different halogen atoms, in each case straight-chain or branched alkoxyalkyl, (di)alkylaminoalkyl or alkylthioalkyl having 1 to 6 carbon atoms in the respective alkyl moieties, straight-chain or branched alkenyl having 2 to 8 carbon atoms, straight-chain or branched halogenoalkenyl which has 2 to 8 carbon atoms and contains 1 to 6 halogen atoms, cycloalkyl which has 3 to 7 carbon atoms or cycloalkylalkyl which has 3 to 7 carbon atoms in the cycloalkyl moiety and 1 to 4 carbon atoms in the straight-chain or branched alkyl moiety, each of these cycloalkyl or cycloalkylalkyl radicals being optionally monosubstituted to tetrasubstituted on the cycloalkyl moiety by identical or different substituents selected from the group consisting of alkyl having 1 to 4 carbon atoms and halogen; $R^1$ furthermore represents phenyl, benzyl or phenethyl optionally monosubstituted to tetrasubstituted on the phenyl moiety by identical or different substituents selected from the group consisting of halogen, cyano, nitro, in each case straight-chain or branched alkyl, alkoxy or alkylthio in each case having 1 to 4 carbon atoms, or in each case straight-chain or branched halogenoalkyl, halogenoalkoxy or halogenoalkylthio in each case having 1 to 4 carbon atoms and 1 to 9 identical or different halogen atoms, $R^2$ represents fluorine, chlorine, bromine or iodine, or represents straight-chain or branched alkyl having 1 to 4 carbon atoms, $R^3$ and $R^4$ independently of one another in each case represent hydrogen, methyl or ethyl, $R^5$ and $R^6$ independently of one another in each case represent hydrogen, in each case straight-chain or branched alkyl having 1 to 10 carbon atoms which is optionally substituted by alkoxy, carboxyl, alkoxycarbonyl or (di)alkylamino having in each case 1 to 10 carbon atoms in the alkyl moieties, or represent straight-chain or branched alkenyl having 2 to 10 carbon atoms, carboxyl, or alkoxycarbonyl having 1 to 4 carbon atoms in the alkyl moiety, phenyl or phenylalkyl which has 1 to 3 carbon atoms in the alkyl moiety and which is in each case optionally monosubstituted to trisubstituted by identical or different substituents selected from the group consisting of halogen, $C_1$-$C_4$-alkyl, $C_1$-$C_4$-halogenoalkyl, $C_1$-$C_4$-alkoxy, $C_1$-$C_4$-halogenoalkoxy, $C_1$-$C_4$-alkylthio, $C_1$-$C_4$-halogenoalkylthio, and pyrrolidinyl ethyl or $R^5$ and $R^6$ together with the carbon atom to which they are bonded form an optionally substituted three- to seven-membered saturated or unsaturated carbocycle, $R^7$, $R^8$, $R^9$, $R^{10}$ and $R^{11}$ independently of one another in each case represent hydrogen, in each case straight-chain or branched alkyl, or alkoxy each of which has 1 to 4 carbon atoms, or in each case straight-chain or branched halogenoalkyl, halogenoalkoxy or halogenoalkylthio in each case having 1 to 4 carbon atoms and 1 to 9 identical or different halogen atoms, and X is oxygen or sulphur.

2. A substituted pyridazinone according to claim 1, in which
$R^1$ represents methyl, ethyl, n- or i-propyl, n-, i-, s- or t-butyl, methoxymethyl, ethoxymethyl, methoxyethyl or ethoxyethyl, methylthiomethyl, ethylthiomethyl, methylthioethyl, ethylthioethyl, methylaminomethyl, methylaminoethyl, dimethylaminomethyl, dimethylaminoethyl, ethylaminomethyl, ethylaminoethyl, dimethylaminomethyl, diethylaminoethyl, or represents halogenomethyl, halogenoethyl, n- or i-butenyl, allyl, n- or i-butenyl or n- or i-pentenyl, or 2-fluoropropen-3-yl, 2-chloropropen-3-yl, 1-chloropropen-3-yl, 1,1-dichloropropen-3-yl, 1-fluoropropen-3-yl, 1,1-difluoropropen-3-yl, 1,2-dichloropropen-3-yl, 1,2-difluoropropen-3-yl, 1,1, 2-trichloropropen-3-yl, or represents cyclopentyl, cyclohexyl, cyclopropylmethyl, cyclopentylmethyl, cyclopentylethyl, cyclohexylmethyl or cyclohexylethyl, each of which is optionally monosubstituted to tetrasubstituted in the cycloalkyl moiety by identical or different substituents selected from the group consisting of fluorine, chlorine, bromine, methyl, ethyl, methoxy, ethoxy, halogenomethyl, halogenoethyl, halogenomethoxy and halogenoethoxy; furthermore represents phenyl, benzyl or phenethyl, each of which is optionally monosubstituted or disubstituted in the phenyl moiety by identical or different substituents selected from the group consisting of fluorine, chlorine, bromine, cyano, nitro, methyl, ethyl, n- or i-propyl, n-, i-, s- or t-butyl, methoxy, ethoxy, trifuoromethyl, difluoromethyl and trifluoromethoxy, $R^2$ represents chlorine, bromine, methyl, ethyl or n- or i-propyl, $R^3$ and $R^4$ independently of one another in each case represent hydrogen, methyl or ethyl, $R^5$ and $R^6$ independently of one another in each case represent hydrogen, methyl, ethyl, n- or i-propyl, n-, i- or t-butyl, n- or i-pentyl, n- or i-hexyl, dimethoxymethyl, carboxyl, methoxycarbonyl, ethoxycarbonyl, n- or i-propoxycarbonyl, n-, i- or t-butoxycarbonyl, 2-carboxy-ethyl, 2-methoxycarbonyl-ethyl, 2-ethoxycarbonyl-ethyl,2-t-butoxycarbonyl-ethyl,4-carboxybutyl, 4-methoxycarbonyl-butyl, 3-diethylaminopropyl, allyl, 1,1-dimethylpropen-3-yl, 1,1-dimethylbuten-4-yl, 2-pyrrolidinyl-ethyl, or phenyl or phenylalkyl which has 1 to 3 carbon atoms in the alkyl moiety, each of these phenyl or phenylalkyl radicals being optionally monosubstituted to trisubstituted on the phenyl by identical or different substituents selected from the group consisting of methyl, ethyl, n- or i-propyl, n-, i- or t-butyl, fluorine, chlorine, bromine, methoxy, ethoxy, trifluoromethyl, trifluoromethoxy, difluoromethoxy and trifluoromethylthio, or $R^5$ and $R^6$ together with the carbon atom to which they are bonded form a cyclopropyl, cyclopentyl, cyclohexyl, cyclohexenyl or cycloheptyl ring, each of which is optionally monosubstituted to trisubstituted by identical or different substituents selected from the group consisting of methyl, ethyl, n- or i-propyl and n-, i- or t-butyl, and $R^7$, $R^8$, $R^9$, $R^{10}$ and $R^{11}$ independently of one another in each case represent hydrogen, methyl, ethyl, methoxy, ethoxy, trifluoromethyl, trifluoromethoxy, or difluoromethoxy, and X represents oxygen or sulphur.

3. A compound according to claim 1, wherein such compound is 2-tert.-butyl-4-chloro-5-[(2,2-dimethyl-(2H)-chromen-6-yl)-methylthio]-3(2H)-pyridazinone of the formula

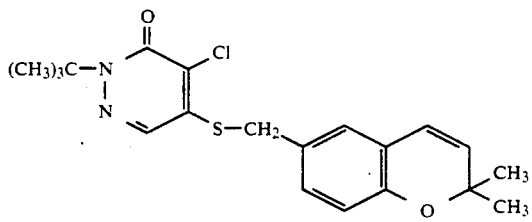

4. A pesticidal composition comprising a pesticidally effective amount of a compound according to claim 1 and a diluent.

5. A method of combating insects and arachnids which comprises applying to such insects and arachnids or to their habitat a pesticidally effective amount of a compound according to claim 1.

6. A method of combating insects and arachnids which comprises applying to such insects and arachnids or to their habitat a pesticidally effective amount of a compound according to claim 3.

* * * * *

UNITED STATES PATENT AND TRADEMARK OFFICE
CERTIFICATE OF CORRECTION

PATENT NO. : 5,141,939

DATED : August 25, 1992

INVENTOR(S) : Weissmuller et al.

It is certified that error appears in the above-identified patent and that said Letters Patent is hereby corrected as shown below:

| | |
|---|---|
| Title Page & Col 1 lines 2 & 3 | Title [54]: Lines 2 & 3 delete " CHROMEN-6-YL-METHYL-OXY-AND-THIAPYRIZINONES " and substitute -- SUBSTITUTED PYRIDAZINONES -- |
| Col. 38, lines 62-63 | Delete " dimethylaminomethyl " and substitute -- diethylaminomethyl -- |

Signed and Sealed this

First Day of March, 1994

Attest:

BRUCE LEHMAN

Attesting Officer

Commissioner of Patents and Trademarks